(12) United States Patent
Streeter

(10) Patent No.: US 6,273,905 B1
(45) Date of Patent: Aug. 14, 2001

(54) METHOD FOR TREATING SPINAL CORD TRANSECTION

(76) Inventor: Jackson Streeter, 3250 Marthiam Ave., Reno, NV (US) 89509

( * ) Notice: Subject to any disclaimer, the term of this patent is extended or adjusted under 35 U.S.C. 154(b) by 0 days.

(21) Appl. No.: 09/346,280

(22) Filed: Jul. 1, 1999

Related U.S. Application Data

(60) Provisional application No. 60/125,690, filed on Mar. 23, 1999.

(51) Int. Cl.$^7$ ..................................................... A61N 5/06
(52) U.S. Cl. .................................. 607/89; 606/9; 606/13; 128/898
(58) Field of Search ............................ 128/898; 607/89, 607/90, 91; 606/21, 3, 9–13; 435/325, 364, 366, 368, 389

(56) References Cited

U.S. PATENT DOCUMENTS

| 4,966,144 | * | 10/1990 | Rochkind et al. | 607/89 |
|---|---|---|---|---|
| 5,445,146 | | 8/1995 | Bellinger . | |
| 5,464,436 | | 11/1995 | Smith . | |
| 5,640,978 | | 6/1997 | Wong . | |
| 5,817,008 | * | 10/1998 | Rafert et al. | 600/323 |
| 5,843,073 | * | 12/1998 | Sinofsky | 606/10 |
| 5,849,585 | * | 12/1998 | Mather et al. | 435/368 |

OTHER PUBLICATIONS

Product List, Thor, 111t, LLLT, Low Level Laser Therapy, Laz., http://www.thorlaser.com/prodlist/index.html, Oct. 6, 1999, pp. 1–4.

Specifications, Thor, 111t, LLLT, Low Level Laser Therapy, low level laser therapy, http://www.thorlaser.com/specs/, Oct. 6, 1999, pp. 1–2.

100mW, Thor, 111t, LLLT, Low Level Laser Therapy, low level laser therapy, Lazer, Thor1., http.thorlaser.com/specs/100m W.html, Oct. 6, 1999, p. 1.

(List continued on next page.)

Primary Examiner—Linda C. M. Dvorak
Assistant Examiner—R. Kearney
(74) Attorney, Agent, or Firm—Polster, Lieder, Woodruff & Lucchesi, LC

(57) ABSTRACT

A method for the treatment of spinal cord transection using low level laser therapy in combination with allogenic implants. In one embodiment, embyronal nerve cells are cultured in vitro and transplanted to a site of spinal cord transection. The site is surgically closed and LLLT applied to a treatment point on the skin adjacent the transection site. To apply LLLT, a therapist applies pressure adequate to blanch the skin at the treatment point, and applies laser energy having a wavelength of about 630 nm to about 904 nm, with laser apparatus having a mean power output of about 100 mW to about 500 mW, at a dosage of about 1 joule/point, up to and including about 30 joules/point. Treatment times, total dosage, and number of treatment points are determined by the therapist or clinician trained in LLLT.

12 Claims, 3 Drawing Sheets

OTHER PUBLICATIONS

200mW, Thor, 111t, LLLT, Low Level Laser Therapy, low level laser therapy, Laser, Thor1., http://www.thorlaser.com/specs/200m W.html, Oct. 6, 1999, p. 1.

500mW, Thor, 111t, LLLT, Low Level Laser Therapy, low level laser therapy, Laser, Thor1., http://www.thorlaser.com/specs/500m W.html, Oct. 6, 1999, p. 1.

200mW, Thor, 111t, LLLT, Low Level Laser Therapy, low level laser therapy, Lazer, Thor1., http://www.thorlaser.com/specs/200m W650nm.html, Oct. 6, 1999, p. 1.

680nm Probe, Thor, 111t, LLLT, Low Level Laser Therapy, low level laser therapy, Lazer., http://www.thorlaser.com/specs/680.html, Oct. 6, 1999, p. 1.

"Lasers In Orthopedic Surgery—Laser Therapy: Scientific Basis and Clinical Role", Jeffrey R. Basford, M. D., Ph.D., May 1993, vol. 16, No. 5, pp. 541–547.

"The Photobiological Basis of Low Level Laser Radiation Therapy", Photobiological Basis of LLLT, Kendric C. Smith, pp. 1–7.

"The Efficacy of Laser Therapy for Musculoskeletal and Skin Disorders: A Criteria–Based Meta–analysis of Randomized Clinical Trials", Physical Therapy/vol. 72, No. 7/Jul. 1992, pp. 483/13–491/21.

"Is Laser Therapy Overtaking Ultrasound?" http://www.laser.uk.com/laser, Therapy vs. ultrasoun.html, dated Feb. 20, 1999.

"Laser Therapy Introduction" http://laser.uk.com/physio.html, Mar. 4, 1999, 12 pgs.

"The use of low power lasers in sports medicine", G.A. Gordon, Clinical Sports Medicine 2, 53–61 (1990).

Low Level Laser Therapy—Clinical Practice and Scientific Backgound, Jan Turner and Lars Hode, Prima Books in Sweden AB 1999, pp. 1–9; 45–58; 59–109; 113–116; 118; 132–134; and 151–156.

* cited by examiner

METHOD FOR TREATING SPINAL CORD TRANSECTION

CROSS-REFERENCE TO RELATED APPLICATIONS

This application claims the benefit of U.S. provisional application No. 60/125,690 filed Mar. 23, 1999.

BACKGROUND OF THE INVENTION

This invention relates generally to laser apparatus and more particularly, to low level laser therapy apparatus.

High energy laser radiation is now well-accepted as a surgical tool for cutting, cauterizing and ablating biological tissue. High energy lasers are routinely used to vaporize superficial skin lesions, to make superficial incisions such as those required for plastic surgery, and to make deep cuts required for major surgical operations. Such lasers accomplish their results thermally, by heating the tissue.

Less well-known is that low levels of laser energy have a non-thermal, biostimulative effect on biological tissues. The therapeutic application of low level laser energy, frequently known as low level laser therapy (LLLT), produces beneficial clinical effects in the treatment of musculoskeletal, neurological and soft tissue conditions. LLLT is non-invasive and avoids the potential side effects of drug therapy. More specifically, LLLT delivers photons to targeted tissue, penetrating the layers of skin to reach internal tissues to produce a specific, nonthermal photochemical effect at the cellular level. Jeffrey R. Basford, *Laser Therapy: Scientific Basis and Clinical Role*, ORTHOPEDICS, May 1993, at 541. In particular, LLLT appears to enhance the regeneration of neural tissue. JAN TUNER & LARS HODE, Low LEVEL LASER THERAPY: CLINICAL PRACTICE AND SCIENTIFIC BACKGROUND (1999).

Known LLLT devices and methods involve the application of laser energy at a wavelength in the near to mid infrared range, under certain limited conditions which limit the dosage of laser energy being applied. Known LLLT devices and methods involve the limited application of laser energy with devices having a very low average power output well below 100 mW. Such devices require extended periods of time to deliver any given dosage to a treatment point. Especially when multiple points are being treated, and multiple treatments required, longer treatment times are a significant inconvenience for both technician and patient. Some LLLT methods involve the application of laser energy to limited, specified sites for specific reasons. For example, known LLLT methods for treating specific pain symptoms involve applying laser energy to specific, charted treatment points which are correlated with the specific pain symptoms. However, such methods are limited to the treatment of specific symptoms, do not identify specific laser energy dosages, and do not provide any guidelines for varying dosages for treatment of a range of tissue injuries.

Curently, spinal cord transection is a devastating injury with no known curative treatment. Patients are more or less paralyzed depending on the spinal level of the transection. While some basic research has been done on regenerating spinal cord neurons in vitro, clinical progress has been slow. As a result, no known methods currently exist to repair spinal cord transection. Therefore, because of the beneficial effect of LLLT on neural regeneration, LLLT presents the basis of a promising new approach to the treatment of severe neural injuries such as spinal cord transection.

It would therefore be desirable to provide improved methods for the treatment of spinal cord transection. It would also be desirable to provide such a method which uses LLLT for its beneficial effect on neural regenartion. It would be further desirable to provide such a method which is relatively inexpensive to implement and easily practiced by trained surgeons.

BRIEF SUMMARY OF THE INVENTION

These and other objects may be attained by a method for treating spinal cord transection which in one embodiment includes the steps of culturing embyronal nerve cells in vitro, transplanting the cultured cells to a transected area of spinal cord, covering the area of transplantation with a fibrin-based membrane, closing the site, and locally applying LLLT to a treatment point on the skin adjacent the site of transection. In one embodiment, the method employs LLLT apparatus having a mean power output of about 100 mW to about 500 mW, and emitting laser energy at a wavelength in the visible to near-infrared range. Dosages per treatment point are from about 1 joule/point, up to and including about 30 joules/point, where one treatment point is spot having a diameter of about 1 cm.

In applying the LLLT, an LLLT trained therapist, such as a clinician or physiotherapist, first determines a dosage within the above range, based on the severity and location of the transection, and the patient's response to LLLT. The therapist then uses a handheld laser probe of the LLLT apparatus to first apply adequate pressure to blanch the skin over the closed transection site. The LLLT apparatus is energized and low levels of laser energy are applied to the treatment point for a treatment time dependent on the dosage determined by the therapist. Total energy dose, number and location of treatment points, and number of treatments are determined by the treating physician.

DETAILED DESCRIPTION OF THE INVENTION

Figure 1:
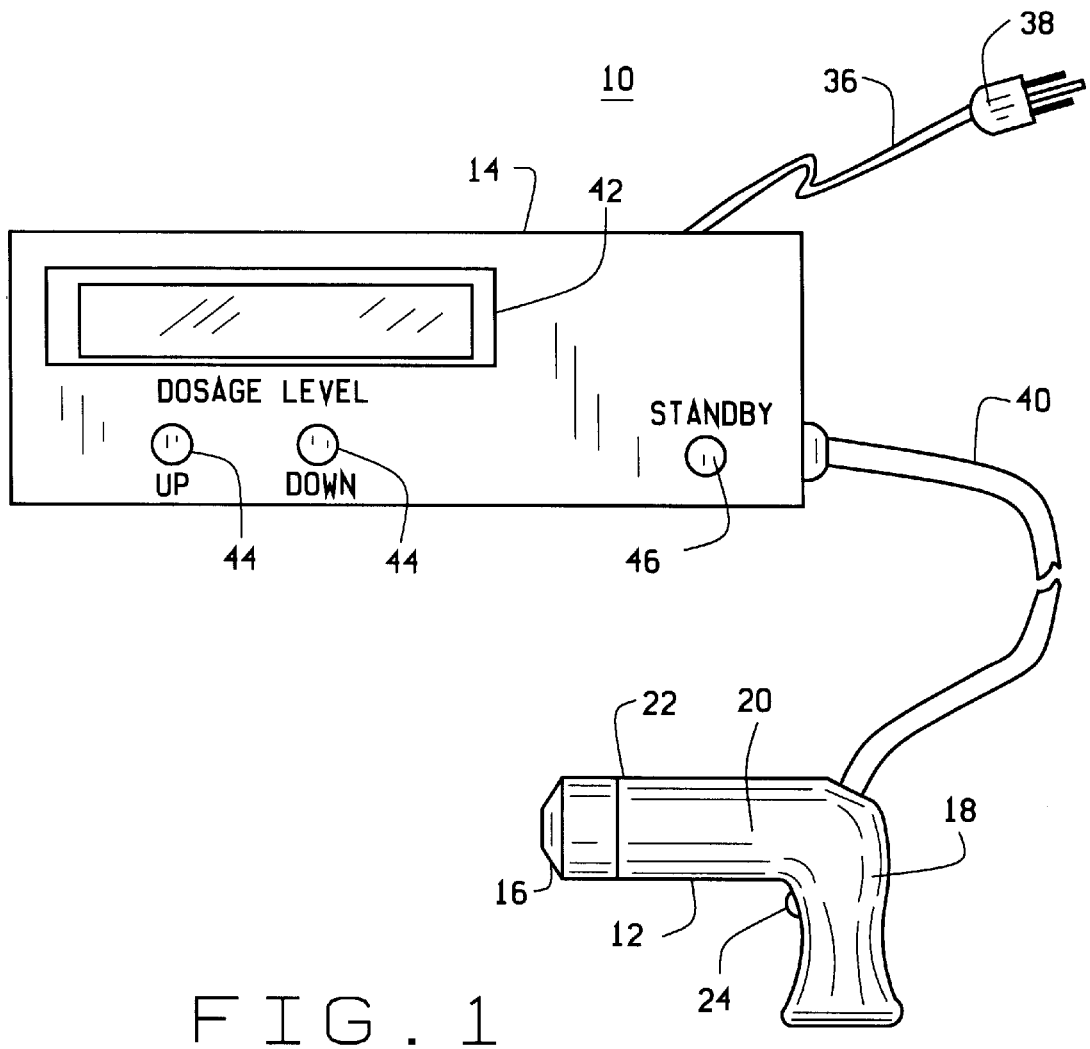
FIG. 1 is a schematic illustration of an LLLT apparatus.

FIG. 1 is a schematic illustration of an LLLT apparatus 10. LLLT apparatus 10 includes a handheld laser probe 12 coupled to a control unit 14. Probe 12 includes a probe head 16 in which laser diodes (not shown in FIG. 1) are mounted. In an exemplary embodiment, four 30 mW laser diodes are mounted in head 16 and angled so that laser beams emitted from the diodes intersect at a short distance away from the head, thus producing a combined mean power output of 120 mW at the point of intersection as described in more detail below. In one embodiment, probe 12 includes a handle portion 18 extending from barrel portion 20 in a substantially pistol-shaped configuration. Head 16 is at a distal end 22 of barrel portion 20. Handle portion 18 and barrel portion 20 are fabricated, for example, from a molded plastic material.

A switch button or trigger 24 is located on handle portion 18. The precise shape of probe 12 is varied among different ergonomic configurations to make repeated and prolonged use of probe 12 more comfortable. For example, in one embodiment handle portion 18 is molded with indentations forming a grip. In an alternative embodiment, probe 12 is a computer mouse-like element having a shape especially suitable for grasping from above, wherein the laser diodes are mounted on a bottom surface and button 24 is located in a position on the mouse-like element which is easily reached with, for example, the index finger. In another alternative embodiment, probe 12 has an elongate, penlight-like shape having two ends, with the laser diode or diodes mounted at one end and button 24 located in a position easily reached with an index finger when probe 12 is grasped as one would typically grasp a pencil.

To limit the dosage of laser energy within a predetermined dosage range, apparatus 10 includes control unit 14 which includes a box housing circuitry for controlling the operation of apparatus 10. An AC power cord 36 with a grounded plug 38 allows unit 14 to be plugged into a conventional electrical outlet. A second power cord 40 couples probe 12 to control unit 14. In an exemplary embodiment, unit 14 includes a display 42, such as an LED readout, for displaying a pre-selected laser energy dosage level in joules/point, a circuit board including a control circuit (not shown in FIG. 1), a microprocessor (not shown in FIG. 1) linked to the control circuit and storing in memory the preselected dosage level, and at least one dosage selection element 44 such as a switch, knob or the like, linked to the control circuit for pre-selecting the dosage level. The control circuit is further linked to the laser diodes. Generally, the control circuit functions to control the delivery of power to the laser diodes according to a predetermined dosage as selected using dosage selection element 44. In one embodiment as shown in FIG. 1, the dosage selection element 44 is a pair of buttons, with an "Up" button for increasing the dosage, and a "Down" button for decreasing the dosage. In an alternative embodiment, the dosage selection element is a single potentiometer, dial or the like for dialing in the preselected dosage. Of course, other implementations of the dosage control element will be obvious to those skilled in the electronics art.

Control unit 14 further includes a locking element 46 for controlling access to, and use of apparatus 10. In an exemplary embodiment as shown in FIG. 1, control unit 14 includes a keyed lock 46 having an OFF position, a STANDBY position and an ON position. The STANDBY and ON positions can only be reached with a matching key (not shown). In the OFF position apparatus 10, including the diodes, is disabled. With the key, and with lock 46 in the STANDBY position, apparatus 10 is enabled for selecting the desired dosage using dosage control element 44. With lock 46 in the ON position and button or trigger 24 depressed, the laser diodes are energized for a period of time calculated by the memory chip to deliver the preselected dosage, the time being dependent on the total power output of the laser diodes.

Figure 2:
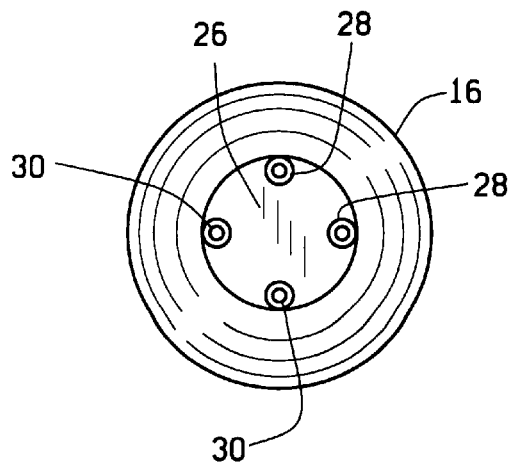
FIG. 2 is a plan view of the low level laser probe head.
Figure 3:
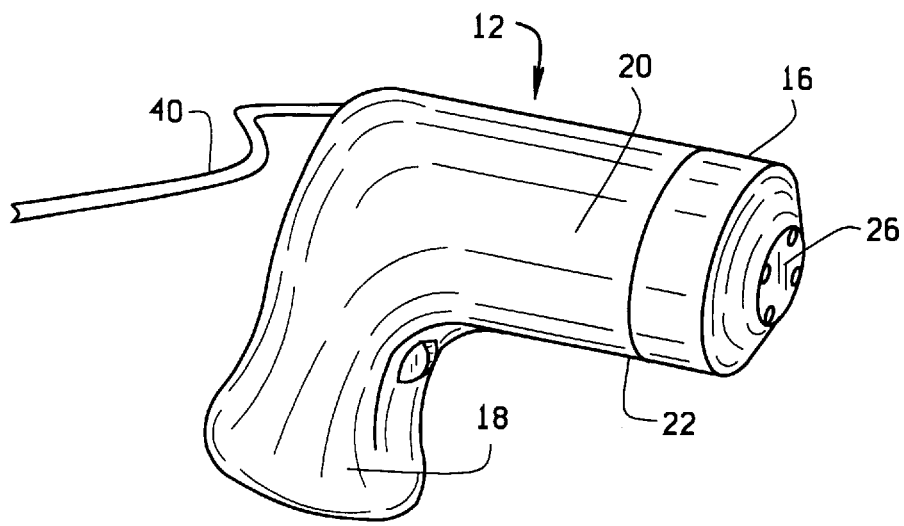
FIG. 3 is a perspective view of a low level laser probe.

FIG. 2 is a plan view of one embodiment of probe head 16. Probe head 16 is substantially cylindrical with a tapered forward end ending in a face 26 having openings 28 from which the laser energy is emitted. FIG. 3 is a perspective view of probe 12 showing more clearly the configuration of probe head 16. Probe head 16 is fabricated from, for example, a metal or plastic material and is coupled to barrel portion distal end 22. In an exemplary embodiment, four 30 mW laser diodes 30 are each mounted in an opening 28 in face 26, and angled so that laser energy beams emitted from each diode substantially overlap or intersect each other at a distance of about 0.5 to about 2.0 cm from face 26 to yield a combined power output of 120 mW in the overlapping area. In one embodiment, diodes 30 are angled in face 26 so that the laser energy beams overlap at a distance of about 1.7 cm from face 26. Generally, diodes 30 are any type which emits biostimulative laser energy, which includes lasers emitting energy at wavelengths between about 630 nm and about 904 nm.

The specific laser diodes chosen depends on the desired wavelength of the emitted laser energy, which depends on a number of factors including cost, as well as the desired level of penetration, and the type of tissue and injury being treated. In addition, some wavelengths appear to be especially suitable for specific applications. For example, low power HeNe lasers emitting at a relatively short wavelength of about 633 nm appear to be especially suited for conditions or injuries requiring lower levels of penetration, such as skin wounds, mucous membranes problems, and eye conditions such as conjunctivitis. However, for most internal tissue injuries amenable to LLLT, a penetration depth of about 2–3 cm is suitable, and is achieved with an intermediate wavelength of about 830 nm, that emitted by GaAlAs laser diodes. In addition to wavelength, the precise number and type of diodes used can be varied, limited only by the requirement that the combined or total mean power output be in the range of about 100 mW to about 500 mW, in pulsed or continuous mode.

Thus, in one embodiment diodes 30 are continuously emitting GaAlAs diodes emitting at a near-infrared wavelength of about 830 nm in a collimated beam. 30 mW GaAlAs diodes are relatively inexpensive, easily commercially obtained, and require only four to provide a mean power output in the range of about 100 mW to about 500 mW. However, higher or lower power GaAlAs diodes, or other biostimulative diodes emitting in the visible to near-infrared wavelength range of about 630 mn to about 904 may be used. For example, in one alternative embodiment, InGaAlP laser diodes are used, emitting at a wavelength of about 630–685 nm. In another alternative embodiment, pulsed GaAs diodes are used, emitting at about 904 nm. In other alternative embodiments, the combined or total power output is varied from about 100 mW to about 500 mW by changing the number and power of diodes used. For example, in one alternative embodiment, a single GAAlAs diode with a power output of 100 mW is used. As explained above, the precise number and type of diodes used is limited only by the requirement that the total power output be in the range of about 100 mW to about 500 mW. However, cost considerations are also a factor in deciding the number and types of diodes employed.

Figure 4:
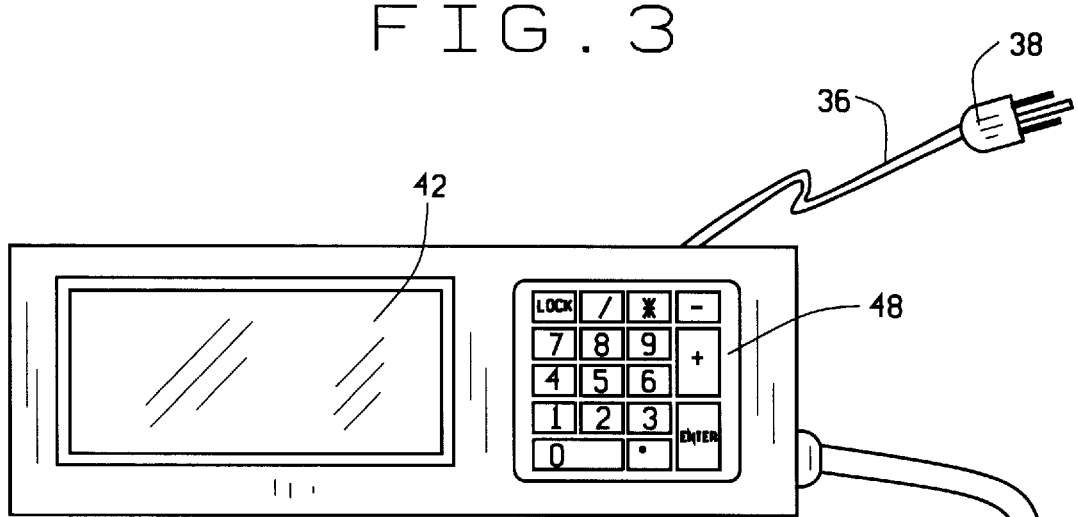
FIG. 4 is a schematic illustration of the LLLT apparatus with a PIN system.
Figure 4:
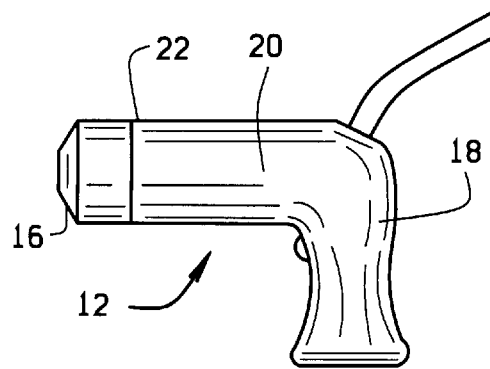

FIG. 4 is a schematic illustration of an alternative embodiment of apparatus 10 in which locking element 46 is implemented with an access code system, such as a personal identification number (PIN) system. The PIN system includes a microprocessor (not shown) included in control unit 14. In this embodiment, control unit 14 includes display 42 and an input device 48 such as a keypad or LCD touch screen for entering data, including PIN's, into the microprocessor. In another alternative embodiment, control unit 14 is communicatively coupled to a compatible computer containing a microprocessor and having its own input device. The microprocessor stores hundreds or thousands of valid multiple-digit PIN's, each associated with a predetermined activation time. The predetermined activation time is a period of minutes sufficient to cover multiple treatments each lasting seconds or minutes. Upon entering a valid PIN, apparatus 10 is enabled to allow dosage selection, and then energizes diodes 30 when button or trigger 24 is depressed. In an alternative embodiment, instead of the PIN system as described above, control unit 14 includes a magnetic card reader for reading a card such as a credit card having a magnetically encoded authorization number for enabling apparatus 10.

As described above, each PIN is associated with a predetermined activation time. With each treatment or use lasting a limited period of seconds or minutes under a given PIN, the microprocessor is programmed to subtract the duration of use, or treatment time, from the activation time remaining on the given PIN. In one embodiment, the treatment time is calculated as the number of seconds or minutes during which diodes 30 are energized. Thus, microprocessor is programmed to keep account of the activation time remaining with each successive use of apparatus 10. For example, in one embodiment each PIN is associated with a total activation time of 100 minutes. With an average treatment time of 10 minutes per treatment, one PIN is used for a total of 10 treatments. Of course, the total number of minutes associated with a single PIN can be varied, as can the use of that time by the PIN holder. In one embodiment, the microprocessor is further programmed to issue a warning displayed on display 42 when a certain limited number of minutes remains in the activation time. For example, the microprocessor is programmed to issue a warning when 10 minutes remains of the total activation time on a given PIN. Of course, the time limit for issuing the warning can be varied.

In one embodiment, valid PIN's are provided via a computer network such as the Internet or Web so that a user of apparatus 10 can purchase activation time electronically. For example, a Web site on a server maintained by the manufacturer or seller of apparatus 10 is linked to a database which stores profile information on each user. A new user first registers with the Web site via a remote computer which is linked to the Web, providing profile information such as name, institution, billing information, and the like. When the profile information has been provided, or accessed from the database after being previously entered, and the user billed for the activation time, a valid PIN number for a predetermined activation time is provided to the user, for example by an automatic e-mail communication to the user, or through a separate Web page. The user then uses the PIN for LLLT treatment until the activation time is exhausted. If desired by the user, additional activation time is purchased in like manner and added, using a separate authorization code, to a previously used PIN so that the user does not need to repeatedly change his or her PIN. Of course, the electronic purchasing system is easily varied to use a magnetically encoded card as described above.

Figure 5:
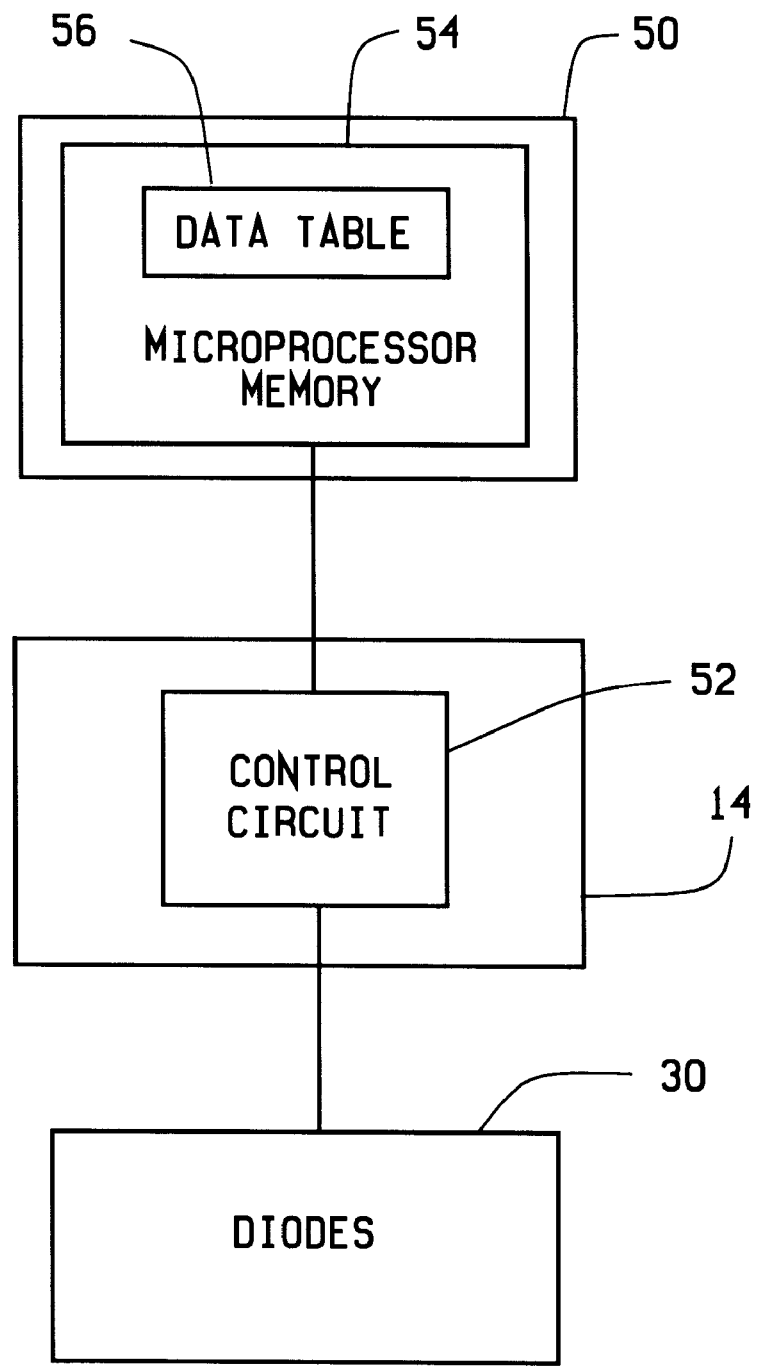
FIG. 5 is a block diagram of the LLLT apparatus.

FIG. 5 is a block diagram of apparatus 10, showing microprocessor 50 coupled to control circuit 52. In one embodiment, microprocessor 50 is programmed to store patient data information for individual patients, so that the user can easily monitor previous LLLT dosages and patient progress. For example, the microprocessor has an on-board memory 54 for storing patient information. In one embodiment, a data table 56 is stored in the microprocessor memory and includes an identifying code for each previous visit (for example the date) and the associated dosage(s), treatment times, codes for treatment locations, and other treatment information from previous treatments. In one embodiment, the patent data information includes a code for specifying the level and location of the patient's pain on each previous visit.

Apparatus 10 is used for treating a variety of tissue injuries, including musculoskeletal injuries, bone fractures, and spinal cord transections, and for improving local microcirculation, particularly cardiac microcirculation. A treatment point is defined as a spot having a diameter of about 1 cm. The laser energy dosage delivered to a treatment point is dependent on both the mean power output of the laser source, and time. Thus, at a given mean power output, the laser energy dosage is determined by the time during which the laser diodes are energized and laser energy is being applied to the treatment point. Generally, a dosage of laser energy from about 1 joule/point, up to and including about 30 joules/point, is chosen by a clinician based on the clinician's experience and training as well as the individual patient's previously demonstrated response to LLLT.

The clinician, or a trained technician, accesses apparatus 10 with a key, PIN, or with a password for accessing a software control package as described above. The select dosage is dialed or otherwise input into control unit 14. With apparatus 10 enabled for the selected dosage, the clinician or technician applies face 26 of probe 12 to a treatment point on the patient's skin surface adjacent the internal tissue to be treated, applying enough pressure with face 26 at the treatment point so that the skin is slightly blanched. This step clears blood from the path of the laser energy to decrease absorption of the laser energy by the blood, thus allowing the greatest depth of penetration through the dermal structures to the internal injury. Button 24 is depressed and laser diodes 30 energized so that laser energy is applied to the treatment point. In one embodiment, multiple treatment points are treated, wherein the treatment points are located in, or at the periphery of, a region of skin adjacent the internal injury. In one embodiment, the treatment points are separated by at least about 1 cm. If necessary, the treatment is repeated at intervals of about 1 to about 3 or 4 days. Number of treatment points and separation of treatment points, as well as the number of repeat treatments, varies with the location and type if injury, as well as the individual patient's response to LLLT.

More specifically, to practice a method for repairing spinal cord transection using LLLT apparatus 10, allogenic embryonal nerve cells are first cultured in vitro according to tissue culture techniques known to those skilled in the art of tissue culture technques. The transected region of spinal cord is maximally exposed by the surgical removal of overlying spinal bony structures. At the site of transection, all debris and fibrinous material is removed. At the now well exposed site of transection, the cultured cells are transplanted into the cleft between the stumps of spinal cord at the transection, filling the cleft. Thus, the transplanted cells form a new connection between the spinal cord stumps. The transection site is covered with a thin, resorbable membrane such as a fibrin-based membrane. The site is then closed in standard surgical fashion.

To promote regeneration of the transplanted cultured neural tissue and thus functional re-connection of the cord stumps, LLLT is applied to a treatment point on the skin adjacent the transection site. An LLLT trained therapist, such as a clinician or physiotherapist, first determines a dosage from about 1 joule/point, up to and including about 30 joules/point. Dosages are based on the location and severity of the transection, and the patient's response to LLLT. The therapist then uses a handheld laser probe of the LLLT apparatus to first apply adequate pressure to blanch the skin at the treatment point. The LLLT diodes are energized as described above and low levels of laser energy are applied to the treatment point for a treatment time dependent on the dosage determined by the therapist. In one embodiment, the LLLT apparatus automatically stops energizing the laser diodes after a treatment time sufficient to deliver the pre-selected dosage. Total energy dose, number and location of treatment points, and number of treatments are determined by the treating physician. In one embodiment, a square grid pattern about 6 cm on a side is projected or otherwise indicated on the skin over the transected region. The square grid pattern is generally centered over the transection site and indicates multiple treatment points separated by about 1 cm. The points of the grid are then used to guide location of each point application of LLLT, thus insuring that the entire transection region is treated. In one embodiment, the grid pattern is used to guide application of LLLT at a dose of 30 J/point, every other day. Overall length of treatment depends on individual patient response, in one embodiment lasts about 2 to about 6 weeks.

Thus, the LLLT methods provide are suitable for treating spinal cord transection, in a way which is believed to repair the transection with a functional neural connection. The method is relatively inexpensive, and simple for trained neurosurgeons to incorporate into current standard of care treatment.

From the embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for treating spinal cord transection, said method comprising the steps of:

culturing embryonal nerve cells in vitro;

transplanting the embryonal nerve cells to a site of spinal cord transection;

surgically closing the site of transection;

applying pressure adequate to blanch the skin at at least one treatment point having a diameter of about one centimeter over the site of transection;

applying to the at least one treatment point laser energy having a wavelength in the visible to near-infrared range, with a laser light source at a mean power of about 100 mW to about 500 mW.

2. A method in accordance with claim 1 wherein applying laser energy having a wavelength in the visible to near-infrared range comprises applying laser energy having a wavelength of about 630 nm to about 904 nm.

3. A method in accordance with claim 1 wherein applying laser energy at the at least one treatment point comprises the step of applying the laser energy for a period sufficient to apply a laser energy dosage of about 1 joule/point to about 30 joules/point.

4. A method of using low level laser therapy, said method comprising the step of using a laser energy source to apply low level laser energy to at least one treatment point having a diameter of about one centimeter on skin adjacent to a site of spinal cord transection having a transplant of embryonal neural tissue, wherein the laser energy has a wavelength of about 630 nm to about 904 nm and the laser energy source delivers the laser energy at a mean power over about 100 mW.

5. A method in accordance with claim 4 further comprising the step of transplanting the embryonal neural tissue into the region of spinal cord transection.

6. A method in accordance with claim 4 wherein said low level laser energy is delivered with laser apparatus having a mean power output of about 100 mW to about 500 mW for a treatment time sufficient to deliver a dosage of about 1 joule/point to about 30 joules/point.

7. A method for treating spinal cord transection, said method comprising the steps of:

transplanting a transplant of embryonal nerve cells into a site of spinal cord transection;

at at least one treatment point having a diameter of about one centimeter on skin adjacent the site of spinal cord transection, applying pressure adequate to blanch the skin;

at the at least one treatment point, using a laser light source to apply laser energy having a wavelength in the visible to near-infrared range at a mean power over about 100 mW.

8. A method in accordance with claim 7 wherein applying laser energy comprises applying laser energy at a mean power up to about 500 mW.

9. A method in accordance with claim 7 wherein applying laser energy having a wavelength in the visible to near-infrared range comprises applying laser energy having a wavelength of about 630 nm to about 904 nm.

10. A method in accordance with claim 7 wherein applying laser energy at the at least one treatment point comprises the step of applying the laser energy for a period sufficient to apply a laser energy dosage of about 1 joule/point to about 30 joules/point.

11. A method in accordance with claim 7 wherein applying laser energy at the at least one treatment point comprises the step of applying the laser energy at a plurality of treatment points.

12. A method in accordance with claim 7 wherein applying to the skin laser energy at a plurality of treatment points comprises the step of applying the laser energy at a plurality of treatment points separated by about 1 cm.

* * * * *